United States Patent
Winston et al.

(10) Patent No.: US 8,834,857 B1
(45) Date of Patent: *Sep. 16, 2014

(54) DEODORIZING AND SKIN CLEANING

(75) Inventors: Anthony E. Winston, East Brunswick, NJ (US); Richard F. Stockel, Bridgewater, NJ (US); Anthony Joseph Sawyer, Albuquerque, NM (US)

(73) Assignee: Nevada Naturals Inc., Albuquerque, NM (US)

(*) Notice: Subject to any disclaimer, the term of this patent is extended or adjusted under 35 U.S.C. 154(b) by 0 days.

This patent is subject to a terminal disclaimer.

(21) Appl. No.: 13/374,856

(22) Filed: Jan. 18, 2012

Related U.S. Application Data

(60) Provisional application No. 61/461,430, filed on Jan. 18, 2011, provisional application No. 61/461,685, filed on Jan. 21, 2011.

(51) Int. Cl.
| | |
|---|---|
| *A61Q 19/00* | (2006.01) |
| *A61Q 19/10* | (2006.01) |
| *A61Q 15/00* | (2006.01) |
| *A61K 31/215* | (2006.01) |
| *C07C 69/02* | (2006.01) |

(52) U.S. Cl.
CPC ............ *A61Q 19/00* (2013.01); *A61K 2300/00* (2013.01); *A61Q 15/00* (2013.01); *A61L 2300/602* (2013.01)
USPC ...... 424/65; 424/70.1; 424/70.11; 424/70.14; 424/70.17; 424/70.22; 424/70.27; 424/70.28; 424/401; 514/162; 514/163; 514/551; 514/579; 514/642; 514/643; 560/1; 560/25; 560/8; 560/129; 564/1; 564/123

(58) Field of Classification Search
USPC .............. 424/65, 70.1, 70.11, 70.14, 70.17, 424/70.22, 70.27, 70.28, 401; 514/162, 514/163, 551, 579, 642, 643; 560/1, 2, 8, 560/129; 564/1, 123
See application file for complete search history.

(56) References Cited

U.S. PATENT DOCUMENTS

| | | | |
|---|---|---|---|
| 3,825,560 A * | 7/1974 | Saito et al. .................... 548/534 |
| 4,234,566 A * | 11/1980 | Packman et al. ................. 424/47 |
| 4,997,851 A | 3/1991 | Isaacs et al. |
| 5,434,182 A | 7/1995 | Isaacs et al. |
| 5,780,658 A | 7/1998 | Martinez-Pardo et al. |
| 6,414,023 B1 | 7/2002 | Brandsborg et al. |
| 6,638,978 B1 | 10/2003 | Kabara |
| 7,074,447 B2 | 7/2006 | Bonaventura et al. |
| 7,087,769 B1 | 8/2006 | Contijoch Mestres |
| 8,193,244 B1 * | 6/2012 | Stockel et al. ................. 514/529 |
| 2004/0122095 A1 | 6/2004 | Bonaventura et al. |
| 2004/0166082 A1 | 8/2004 | Urgell-Beltran et al. |
| 2004/0175350 A1 | 9/2004 | Urgell Beltran et al. |
| 2004/0254232 A1 | 12/2004 | Beltran et al. |
| 2004/0265443 A1 | 12/2004 | Beltran et al. |
| 2005/0084471 A1 | 4/2005 | Andrews |
| 2005/0175747 A1 | 8/2005 | Seguer Bonaventura et al. |
| 2006/0030512 A1 | 2/2006 | Hart |
| 2007/0086977 A1 * | 4/2007 | Stockel ...................... 424/78.27 |
| 2009/0318557 A1 * | 12/2009 | Stockel ......................... 514/565 |
| 2010/0056528 A1 * | 3/2010 | Yacovan et al. ............ 514/238.2 |
| 2010/0056628 A1 * | 3/2010 | Stockel et al. ................. 514/551 |
| 2010/0173993 A1 | 7/2010 | Sawyer |
| 2010/0203005 A1 * | 8/2010 | Bettle, III ................. 424/78.07 |
| 2010/0328544 A1 * | 12/2010 | Hendrickson et al. ......... 348/726 |
| 2012/0328544 A1 * | 12/2012 | Stockel et al. .................. 424/61 |

FOREIGN PATENT DOCUMENTS

| | | |
|---|---|---|
| EP | 1414394 B1 | 6/2009 |
| WO | WO/2008/014824 | 2/2008 |

* cited by examiner

*Primary Examiner* — Jane C Oswecki
(74) *Attorney, Agent, or Firm* — Posz Law Group, PLC

(57) ABSTRACT

A method for cleaning, benefiting, or deodorizing skin or hair utilizing a body wash, skin cleaner, soap, shampoo or deodorizer formulation containing a controlled release skin benefit or deodorizing salt, a hydrophilic moisturizing polymer and surfactants is described. The method imparts benefits or deodorizing agents to the skin or hair and maintains effective levels for an extended period.

10 Claims, No Drawings

DEODORIZING AND SKIN CLEANING

REFERENCE TO RELATED APPLICATIONS

This application claims the benefit of provisional application Ser. No. 61/461,430 filed Jan. 18, 2011. This application claims the benefit of provisional application Ser. No. 61/461,685 filed Jan. 21, 2011. The disclosures of all of the foregoing applications are incorporated by reference herein in their entirety.

FIELD OF THE INVENTION

The present invention provides a method for cleaning, benefiting or deodorizing the skin or hair utilizing formulations that contain a controlled release salt and which provide long lasting benefits to the skin. Formulations of the invention can be used as hand and body soaps, shampoos, body washes, bath products, shower products, deodorants, hand sanitizers, pre-operative scrubs, wound cleaners and the like.

BACKGROUND OF THE INVENTION

Many different skin cleaning and deodorant products are available in the market. Many of these products are formulated to provide various skin benefits or for deodorization of the skin. These products are available in a variety of product forms such as solutions, suspensions, creams, solid sticks, roll-on liquids and aerosol or non-aerosol sprays. Virtually all of these formulations instantaneously release all of their active agents and hence are often used up or depleted within a short period. It is often problematic to provide higher concentrations of actives to extend the effectiveness of formulations, due to the potential for skin irritation or other adverse effects. Accordingly, there is a need for methods which provide longer lasting skin benefits or deodorization. This invention provides a method of cleaning, benefiting or deodorizing the skin or hair using controlled release salts, which provide a reservoir of ions which can benefit or deodorize the skin. The controlled release salts thus maintain a long term skin benefit or extended deodorization activity.

In our co-pending applications we have described various controlled release salts and complexes for various applications on surfaces including skin and hair for both human and animal use. These salts and complexes are formed from cationic and anionic moieties either or both of which can provide benefits when released. The solubility of the controlled release salts is such that when exposed to moisture, the active anionic or cationic portions of the salt, responsible for skin benefits, are released in sufficient quantity to provide their desired beneficial effect, while at the same time leaving sufficient residual undissolved salt to act as a reservoir for the controlled release of additional active ionic portions from the salt as the dissolved skin-benefit agents are depleted. One aspect of our invention is the use of green and natural sources of raw materials.

SUMMARY OF THE INVENTION

The present invention provides a method of cleaning, or deodorizing the skin or hair by applying formulations which provide long lasting benefits. The method of this invention comprises applying a formulation comprising a controlled-release, undissociated, adherent salt, which releases skin or hair benefit or deodorizing agents when it partially dissolves in moisture present on the skin or hair. In addition, formulations of the invention may comprise hydrophilic humectant polymers, one or more surfactants, an emollient glycerol ester of a fatty acid, a buffer or water. In a preferred embodiment of the invention natural or naturally derived ingredients are used and the controlled release, skin or hair adherent salt is derived from a natural amino acid and fatty alcohols or fatty acids from renewable sources.

During application of the skin cleaning and deodorant formulations of the invention, the limited-solubility undissociated controlled-release salt is deposited on the surface of the skin. The controlled release salt partially dissolves and dissociates in the sweat or other moisture present on the skin, releasing skin benefit or deodorizing cations and anions. However, sufficient undissolved, undissociated salt remains on the skin to act as a reservoir to provide extended deodorization and skin benefits from additional ions that are released from the salt at the same rate that the dissolved ions are used up or depleted.

DETAILS OF THE INVENTION

The skin cleaning and deodorizing formulations of this invention comprise (1) from about 0.02 wt % to 5 wt % of a controlled release skin benefit or deodorizing salt with a solubility of less than 2 wt %, preferably equal to or less than 1 wt % and greater than about 0.01 wt % and comprising (i) a surface active cation having both a hydrophobic and a hydrophilic component and (ii) a carboxylate or phenolate anion, (2) optionally from about 0.05% to about 20 wt % of a water absorbing hydrophilic polymer with a molecular weight above 2000, (3) optionally from about 1% to about 90 wt % of an anionic, nonionic or amphoteric surfactant or soap, (4) optionally from about 0.02 to about 2 wt % of an emollient/emulsifier comprising a glycerol ester of a $C_8$-$C_{14}$ fatty acid (5) optionally buffers to provide a pH between about 3.0 and 7.0 and (6) optionally from about 2% to about 95 wt % moisture. Other ingredients can be added to formulations of the invention. These include but are not limited to a suspending agent, a carrier liquid, moisturizers, humectants, emollients, an antiperspirant active, vitamins, dyes, fragrances, thickening agents, processing aids, preservatives and the like.

As noted above the controlled release salt has limited solubility of less than 2 wt %, preferably equal to or less than 1 wt % and greater than about 0.01 wt %. The limited solubility property of the controlled release salt is key to its effectiveness in formulations of this invention. First of all, during product use, much of the delivered undissociated salt remains on the surface of the skim. Secondly, once on the skin, the controlled-release salt needs to have sufficient solubility in the moisture on the skin to release an effective quantity of component skin-benefit ions, while leaving enough undissolved salt on the skin to provide a reservoir of skin benefit ions for release as the dissolved skin benefit ions are used up or dissipated.

The solubility and the amount of moisture on the skin determine how much of the skin benefit ions are released from the controlled release salt. The solubility can be adjusted by varying the molecular weight of the component ions, as well as the hydrophobicity or hydrophilicity of either of the cationic and anionic components. An ion with a higher molecular weight will generally result in a decrease in the solubility of the combined salt and thereby decrease the release of its skin benefit agents from the salt. Salts made from ions with more or larger hydrophobic portions, will also tend to decrease the solubility of the controlled release salt. On the other hand, salts made from ions with more or larger hydrophilic groupings, for example polyhydric alcohols groupings, will tend to increase the salt's solubility. Lower solubility salts will tend to have an increased ability to plate out on skin surfaces and remain there during formulation use. Higher solubility salts will generally have a greater tendency to dissolve in any available moisture during use and to be depleted from the area of application by sweat from the skin. The solubility of the controlled release salt also needs to be appropriate for optimum release of benefit agents to the skin. Thus, it needs to be sufficiently soluble to release an effective level of the dissociated skin benefit ions, yet sufficiently insoluble to leave a reservoir of undissolved skin benefit ions for subsequent release as the skin benefit ions are used up.

Without being limited by these benefits, either or both of the skin benefit anions and cations can be the ones to provide cosmetic, medicinal, cosmeceutical or deodorization benefits to the skin. Cationic agents are often useful in providing skin conditioning, skin smoothing, anti-allergy activity, deodorization and antimicrobial activity etc. Anionic agents often provide vitamins, anti-inflammatories, anti-aging benefits, antimicrobial activity, moisturization, exfoliation, deodorization etc. Cationic and anionic skin benefit agents can be combined into a single controlled release salt to provide agents with multiple long lasting skin benefits. Alternatively a cationic skin benefit agent or an anionic skin benefit agent can be combined with an inactive counter-ion for other reasons, such as to provide for improved adherence to the skin or to modify the controlled release characteristics of the salt.

The controlled release salts of the invention can comprise salts formed of monomeric anions and monomeric cations, monomeric anions and polymeric cations, polymeric anions and monomeric cations or from polymeric anions and polymeric cations.

As noted skin cleaning, and deodorizing formulations of this invention contain from about 0.02% to 5% of the controlled-release, skin-benefit or deodorizing salt, which consists of cationic and anionic components. The cationic components of the controlled-release salt comprise primary ammonium, secondary ammonium, tertiary ammonium, quaternary ammonium, guanidinium or biguanidinium cations. The anionic components comprise carboxylate or phenolate anions.

Some non-limiting examples of controlled release salts include carboxylate and phenolate anions in combination with antimicrobial ($C_8$-$C_{18}$) alkyl dimethyl benzyl ammonium cations, ($C_8$-$C_{18}$), dialkyl methyl benzyl ammonium cations, ($C_8$-$C_{18}$) dialkyl dimethyl ammonium cations, benzalkonium cation, benzethonium cations, sanguinarium cations, cetylpyridinium cations and hexetidinium cations. Useful antimicrobial biguanidinium cations include chlorhexidinium, alexidinium, and polyhexamethylene biguanidinium ions. The antimicrobial properties of these ions can be useful in treating superficial skin infections, for deodorization or for skin sanitization for example.

It is highly preferred to use a controlled-release skin-benefit or deodorizing-salt in which the cationic portion is natural or naturally derived. For example, it is preferred that the hydrophilic part of the cationic portion of the controlled release skin benefit or deodorizing salt be derived from a natural nitrogen-containing compound selected from one of the following an amino acid, a peptide, carnitine, choline, creatine and glycine betaine. All of these compounds have at least one primary amine, quaternary ammonium or guanidine group. Choline has a quaternary ammonium group and an alcohol group but no free carboxylic acid groups. Carnitine and glycine betaine each have a quaternary ammonium group, carnitine has both a hydroxyl group and carboxylic acid group, while glycine betaine has a carboxylic acid group but no alcohol group. Creatine has a guanidinium group and a carboxylic acid group. All amino acids and peptides have at least one amine group and at least one carboxylic acid group. The amino acids, threonine and serine and some peptides, also have an alcohol group.

Water soluble cationic molecules, sometimes referred to as hydrophiles, depend on the presence on water soluble groups in the molecule which may be ionic or non-ionic. Cationic groups include nitrogen groups such as those disclosed in this invention. Ionic groups are very effective, such as the nitrogen cationic functionalities of this invention, as being sufficient to solubilize a C12 hydrocarbon chain. It has been reported in the literature that two cationic protonated nitrogen groups will substantially solubilize a C18 hydrocarbon chain.

Examples of preferred amino acids for preparing cationic skin-benefit or deodorizing salts include glycine, leucine, isoleucine, lysine, arginine methionine, alanine, phenylalanine, tryptophan, valine, asparagint, cysteine, glutamine, proline, tyrosine, histidine, serine, threonine, ornithine, aspartic acid, glutamic acid and taurine.

While, as noted above, it is preferred to use natural amino acids, peptides, choline, carnitine, creatine or glycine betaine to prepare salts of the controlled-release skin-benefit or deodorizing salt of the invention, synthetic amino acids, peptides, choline, carnitine, creatine or glycine betaine, could be used. Natural amino acids are L-amino acids. However synthetic L-amino acids, D-amino acids or racemic mixtures of L- and D-amino acids would be equally effective in performance. Of course, while the production of synthetic compounds might not be quite as environmentally desirable as using naturally sourced renewable raw materials, the resulting cationic surface active derivatives are likely to possess most of the benefits possessed by their natural counterparts.

The hydrophobic portion of the cationic component of the controlled-release skin-benefit or deodorizing salt can range in chain length from 6 to 24 carbons. Preferably it is a naturally derived $C_8$ to $C_{18}$ fatty alcohol or fatty acid. Preferred are those that are made from renewable vegetable sources, such as plants and trees and not from synthetic or oil sources. Non-limiting examples of naturally sourced fatty alcohols are octyl, decyl, lauryl, myristyl, palmityl, cetyl, or stearyl alcohol. Non-limiting examples of naturally sourced fatty acids are caproic, caprylic, lauric, myristic, palmitic, stearic, oleic, linolenic (omega-3 fatty), and linoleic (omega-6 fatty) acids. Natural-sourced alcohols and acids contain only even numbers of carbon atoms. Compounds based on natural renewable-sourced ingredients are generally safer to humans, being completely metabolized by the body to non-toxic compounds, like carbon dioxide and water. They are also more fully biodegraded in the environment and do not leave environmentally undesirable residues. Many of the skin benefit and deodorizing esters and amides of the invention have lower cyto-toxicity than conventional surfactants and are therefore less irritating to the skin, eyes and mucosa. However synthetic alcohols and acids, which include odd numbers of carbon atoms, could also be used to produce the controlled-release surface active skin benefit or deodorizing salts.

Omega-3 fatty acids include α-linolenic acid (ALA), eicosapentaenoic acid (EPA), and docosahexaenoic acid (DHA), all of which are polyunsaturated. Common sources of omega-3 fatty acids include fish oils and plant oils such as flaxseed oil, algal oil and hemp seed oil. Mammalian brains, a delicacy in some parts of the world, are also a rich source of omega-3 fatty acids, and DHA in particular. Mammals cannot synthesize omega-3 fatty acids, but have a limited ability to form the "long-chain" omega-3 fatty acids EPA (20-carbon atoms) and DHA (22-carbon atoms) from the "short-chain" eighteen-carbon omega-3 fatty acid ALA.

A cationic skin benefit or deodorizing ester or amide can be made by esterification or amidization of choline, creatine, carnitine, glycine betaine, an amino acid or a peptide with fatty alcohols or fatty acids. In essence, carboxylic acid groups on the hydrophilic precursor can be esterified with a $C_8$ to $C_{18}$ fatty alcohol to produce a cationic skin-benefit or deodorizing surfactant ester. Alternatively, alcohol groups on the hydrophilic precursor can be esterified with a $C_8$ to $C_{18}$ fatty acid producing a cationic skin-benefit or deodorizing surface-active ester. Cationic skin-benefit or deodorizing amides are prepared from hydrophilic precursors with more than one cationic group by amidization of an amine group. Any carboxylic acid groups are then esterified with either a short or long chain alcohol.

Thus one range of examples of naturally derived controlled release skin benefit or deodorizing salts suitable for formulations of this invention are carboxylate or phenolate salts of cationic esters or amides derived from the esterification or amidization of an amino acid, a peptide, choline, creatine, carnitine or glycine betaine with a fatty alcohol or fatty acid. Examples are carboxylate or phenolate salts of one of the following (i) a cationic $C_8$-$C_{18}$ alkyl ester of a mono-carboxylic amino acid, such as a $C_8$-$C_{18}$ alkyl ester of glycine, leucine, iso-leucine, lysine, arginine, methionine, alanine, phenylalanine, tryptophan, valine, asparagine, cysteine, glutamine, proline, tyrosine, histidine, serine, threonine and ornithine, (ii) a cationic $C_8$-$C_{18}$, $C_2$-$C_{18}$ di-alkyl ester of a di-carboxylic amino acid, such as a dialkyl ester of aspartic or glutamic acid (iii) a cationic $C_8$-$C_{18}$ alkanoate, $C_1$-$C_8$ alkyl diester of serine or threonine, such as a ($C_8$-$C_{18}$)-acyl-($C_2$-$C_8$)-alkyl serinate, a ($C_8$-$C_{18}$)-acyl-($C_2$-$C_8$)-alkyl threonate, a ($C_2$-$C_8$)-acyl-($C_8$-$C_{18}$)-alkyl serinate and ($C_2$-$C_8$)-acyl-($C_8$-$C_{18}$)-alkyl threonate (iv) a cationic an acyl amide-$C_1$-$C_8$ alkyl ester of an amino acid having a free-cationic moiety such as an $N^\alpha$-($C_8$-$C_{18}$) acyl arginine alkyl ($C_1$-$C_8$) ester, (v) a peptide esterified with a $C_8$-$C_{18}$ fatty alcohol or fatty acid and having at least one free cationic moiety, and (vi) a $C_8$-$C_{18}$ alkanoate ester of choline, (vii) a $C_8$-$C_{18}$ alkyl creatinate, (viii) $C_8$-$C_{18}$ alkyl carnitinate or (ix) $C_8$-$C_{18}$ alkyl glycinate betaine.

A particularly preferred group of controlled release salts of carboxylate or phenolate anions with naturally derived multifunctional skin benefit cations include the cations of $N^\alpha$-($C_8$ to $C_{18}$) acyl amide ($C_1$ to $C_8$) alkyl ester of an amino acid having a free-cation moiety. Non-limiting examples of suitable cations of these salts include those of $N^\alpha$-($C_8$-$C_{18}$) acyl arginine alkyl ($C_1$-$C_8$) ester, $N^\alpha$-($C_8$-$C_{18}$) acyl lysine alkyl ($C_1$-$C_8$) ester, $N^\alpha$-($C_8$-$C_{18}$) acyl histidine alkyl ($C_8$-$C_8$) ester, $N^\alpha$-($C_8$-$C_{18}$) acyl trytophan alkyl ($C_1$-$C_8$) ester and $N^\alpha$—($C_8$-$C_{18}$) acyl ornithine alkyl ($C_1$-$C_8$) ester. A preferred sub-group includes the guanidinium cations of $N^\alpha$-($C_8$-$C_{18}$) acyl arginine alkyl ($C_1$-$C_8$) esters. A particularly preferred guanidinium cation is that of $N^\alpha$-lauroyl arginine ethyl ester.

A particularly preferred group of salts combine cations of $N^\alpha$($C_8$-$C_{18}$) acyl arginine ethyl ester salts with anions of ($C_8$-$C_{18}$) fatty acids. These salts are naturally derived, non-toxic, have low cytotoxicity and are very mild to skin. The laurate salt of $N^\alpha$-($C_8$-$C_{18}$) lauroyl arginine ethyl ester is a particularly useful example of a controlled-release salt which delivers a skin conditioning, skin smoothing emollient.

Examples of polymeric cationic components of the controlled release skin benefit or deodorizing salt include cations of polyamines, cations of a polyethyleneimines, polyammonium cations and polyquaternium cations.

The anionic portion of the controlled release salt is as important as the cationic portion. The anionic portion of the salt can be selected on the basis of benefit to the skin or to the solubility of the resulting salt or its ability to promote adherence to surfaces. The anionic portion of the controlled release salt is either a carboxylate or phenolate ion. The anions may have single or multiple anionic functionality and may have additional functional groups. Preferred anions are natural or naturally derived.

One group of useful mono-carboxylate ions are those of fatty acids with between about 6 and 24 carbons. In general those with between 8 and 18 carbons are preferred. A function of such anions could be to reduce the solubility of the controlled release skin benefit molecule and to increase its adherence to the skin. In this regard, the solubility of the controlled release salt generally decreases with increasing chain length of the fatty carboxylate anion. On the other hand fatty carboxylates may also provide other skin benefits. For example, some fatty acids such as undecylenic acid are known to provide antifungal activity.

Di- and tri-carboxylate counter ions, like malate, tartrate, succinate, fumarate, maleate and citrate often greatly decrease the solubility of cationic skin benefit and deodorizing ingredients because the salt can form with more than one cation to each anion.

Carboxylic acids with other functional groups are also useful in formulations of the invention. For example, alpha-hydroxy carboxylates, beta-hydroxy carboxylates, and hydroxy-carboxylates are useful as skin exfoliating agents with formulations that are buffered in the acidic pH range. Non-limiting examples of alpha hydroxy carboxylate ions are glycolate, lactate, malate, tartrate, citrate ions. The acids of several beta hydroxy carboxylates can also provide beneficial activity on the skin. Salicylic acid is an exfoliant and is useful in treatment of acne. It also has some anti-aging effects on the skin. Furthermore it is useful in the removal of corns and warts. Carnitine is another useful betahydroxy carboxylic acid having some anti-oxidant properties. When alpha or beta hydroxy carboxylate ions are released into water from the controlled release salts they can equilibrate with hydrogen ions to form some amount of undissociated acid with the amount dependent on the pH. It is often this dissolved undissociated acid which is responsible for any skin benefits due to the anionic portion of the controlled release skin salt.

There are several other cosmeceutical skin benefit acids which can used as the anionic portion of controlled release salts of the invention. Two non-limiting examples are ascorbic acid and retinoic acid (vitamin A). Ascorbic acid is an alpha hydroxy acid with exfoliant properties but it is also an antioxidant and is claimed to have various skin benefit properties such as anti-aging etc. Retinoic acid is claimed to combat wrinkles and make the skin more youthful.

The anions of polycarboxylate acids like carbomers, polyacrylates, alginates, and the like are useful as anionic counterions for skin benefit cations. These anions are especially effective in increasing adherence of the controlled release salts to the skin. Many of these materials also have moisturizing effects on the skin. Non-limiting examples of useful carboxylates are straight chain and cross linked polyacrylates, and the anions of poly(methylvinylether/maleic acid). Polyacrylic acids, which ionize and form polyacrylates in water, are known as carbomers. Some polyacrylates are marketed under the trade name of Carbopol®. Various Poly(methylvinylether/maleic acid) polymers are marketed under the Trade name of Gantrez®. Additionally alginates, and carboxylated celluloses can be useful.

Another group of useful anions are those of phenols many of which provide exfoliant or antimicrobial activity. Some phenols are used in deep skin peel treatments used to treat blotchy skin, to smooth out coarse wrinkles and to remove precancerous growths. Examples of anions with antimicrobial properties are the phenolate anions of phenol, resorcinol, parachlorophenol, triclosan and parachlorometaxylenol and thymol. Polyphenols and derivatives thereof may also be useful skin benefit agents, for example they exhibit antioxidant properties which can protect the skin against the effects of oxygen exposure and aging. Polyphenols are a group of chemical substances found in plants and are characterized by the presence of one or more phenolic units. For the purpose of this invention, the term phenolate can refer to natural or synthetic molecules that contain one of more hydroxy groups attached to an aromatic ring. Examples of suitable polyphenols are ferulic acid, reservatrol, gallic acid, coumaric acid, catechin, caffeic acid, vanillic acid, chlorogenic acid, aplanin and sinapyl arbutin. Additional useful anionic components are the pentacyclic triterpenoids, e.g. pentaphenyltriterpenes such as betulinic acid, moronic acid, ursolic acid and oleanolic acid.

The controlled release salts of the invention can be produced by any suitable method such as a double decomposition reaction between soluble salts or by direct reaction between an anionic acid and cationic base. The controlled salts of the invention can be added as an ingredient or may be formed in situ in the formulation. Alternatively the product can be formulated as two separated phases, one containing the anionic acid or a soluble salt of the anion and the second phase containing the cationic base or a soluble salt of the cation. The controlled release salt is then formed when the two phases are applied to the skin and are mixed.

An important aspect of the invention is the limited solubility of the undissociated salt. Thus once the surface moisture is saturated with dissociated ions of the controlled release salt, the salt itself does not dissolve. This assures that the undissociated salts of the invention remain on the surface of the skin until one or other of the dissociated ions is used up, or lost. Also since the undissociated salt does not dissolve, it does not penetrate the skin.

For some formulations, an important component of the invention is a water-absorbing hydrophilic polymer with a molecular weight above 2000. Hydrophilic polymers act as skin substantive humectants and provide for moisture to be present on the skin. This moisture layer allows some of the controlled release salt to dissociate, releasing skin benefit or deodorizing agent. For this purpose, generally from about 0.05% to about 20% of hydrophilic polymer is required in formulations of the invention. Suitable hydrophilic polymers include polyacrylates, alginates, and cellulose derivatives such as hydroxyalkyl cellulose of which methyl, hydroxyethyl and, hydroxypropyl cellulose are the most useful. Also useful are gelatin, polydextrin, polyvinyl alcohol. Especially useful for this invention are hydrophilic copolymers known as "super slurpers" which are saponified starch-graft polyacrylonitrile copolymers. These are especially useful since small amounts of super slurper can hold larger amounts of moisture, generally more than their own weight.

Especially useful hydrophilic polymers for increasing the moisture layer on skin are quaternized hydroxypolymers. Without being limited, specific examples include quaternized hydroxypolymers including quaternary ammonium derivatives of hydroxyethyl cellulose, such as polyquaternium-4 and polyquaternium-10. Also useful are polyglycosamineglycan polymers. Cationic guar gums are also effective, including, for example, guar hydroxypropyltrimonium chloride. These polymers not only retain moisture but are also highly effective skin conditioners. Many proteins and polypeptides with molecular weights above about 2000 are also useful for attracting and retaining moisture on the skin and in addition provide skin conditioning benefits.

Another group of useful polymers for attracting and retaining moisture on the skin are categorized as glycosaminoglycans and derivatives thereof. These polymers are natural or naturally derived. An important example of such a polymer is hyaluronic acid, which also provides skin lubricity. Another example is chitosan which has muco-adhesive properties.

Skin cleaning, body wash, shampoo and soap formulations of this invention contain from about 1% to about 90% of one or more anionic, nonionic or amphoteric surfactants or soaps. Surfactants and soaps are used to effectively clean the skin as well as to create foam which enhances the cleaning experience. Furthermore, surfactants and soaps disperse or emulsify the controlled release salts of the invention. While dispersion or emulsion of the controlled-release salt is usually desirable, it is preferred that micro-emulsions of the controlled-release salt not be formed, because this can reduce the tendency of the controlled release salt to be deposited on the skin.

It is desirable to use surfactants and soaps which are non-toxic and mild to the skin. It is preferred to use surfactants and soaps derived from natural plant sources rather than from synthetic or oil derived compounds. Plant sources are generally renewable and are likely to be safer to humans, being completely metabolized by the body to non-toxic compounds, like carbon dioxide and water. They are also more fully biodegraded in the environment and do not leave environmentally toxic residues.

Non-limiting examples of useful anionic surfactants include alkali metal and ammonium salts of acyl sarcosinates, isethionates, methyl taurates, glutamates, lactylates and glycinates. Specific examples are the sodium salts of lauroyl, cocoyl, myristoyl, palmoyl and stearoyl sarcosinate, the sodium salts of sodium salts of lauroyl, cocoyl, myristoyl, palmoyl and stearoyl isethionate, the sodium salts of lauroyl, cocoyl, myristoyl, palmoyl and stearoyl methyl taurate, the sodium salts of lauroyl, cocoyl, myristoyl, palmoyl and stearoyl glutamate, the sodium salts of lauroyl, cocoyl, myristoyl, palmoyl and stearoyl lactylate and the sodium salts of lauroyl, cocoyl, myristoyl, palmoyl and stearoyl glycinate.

Also useful are the alkali metal and ammonium salts of alkyl sulfates, alkyl ether sulfates, alkyl phosphates and alkyl sulfoacetates. Specific examples of these surfactants are sodium lauryl sulfate, sodium cocosulfate, sodium laureth-3 sulfate, sodium mono-lauryl phosphate, sodium lauryl sulfoacetate and sodium myristyl sulfoacetate.

Additional examples include the alkali metal and ammonium salts of sulfated monoglycerides, sulfonated olefins, alkyl aryl sulfonates, primary or secondary alkane sulfonates, alkyl sulfosuccinates, alkyl glycerylether sulfonate, sulfonated methyl esters, sulfonated fatty acids, alkyl ether carboxylates, acyl lactylates, sulfonated olefins, alkyl aryl sulfonates, primary or secondary alkane sulfonates, acylated peptides, alkyl ether carboxylates, sulfated monoglycerides, sulfonated olefins, alkyl aryl sulfonates, An especially mild group of anionic surfactants include the alkali metal and ammonium hydroxypropyl sulfonate alkyl glucoside crosspolymers. The alkyl group can for example be decyl, lauryl, cocoyl, palmityl and cetyl groups.

Another group of useful anionics are classified as "soaps". Soaps are alkali metal or ammonium salts of fatty acids with chain lengths containing between about 8 and 18 carbon atoms. Preferred are those made from natural renewable preferably plant based sources. Non-limiting examples of suitable soaps include alkali metal and ammonium salts of fatty acids such as lauric, myristic, palmitic, stearic, oleic, and linoleic acids.

Suitable nonionic surfactants include but are not limited to $C_8$-$C_{18}$ alkyl glucosides and polyglucosides as well as the sucrose esters of fatty acids. Particularly preferred are the $C_8$-$C_{14}$ alkyl polyglucosides and the sucrose, glucose, sorbitol, sorbitan and polyglycerol esters of $C_{10}$-$C_{18}$ fatty acids. Amine oxides are also useful because of their high foaming action. Additionally polyhydroxy fatty acid amides, alkoxylated fatty acid esters, ethoxylated and ethoxylated propoxylated alcohols as well as ethoxylate-propoxylated block co-polymers can be used. Also useful are alkanolamides and monoglycerides of fatty acids.

Suitable amphoteric surfactants include but are not limited to alkali metal and ammonium alkyl amphoacetates, such as sodium lauroamphoacetate and disodium lauroampho-diacetates, sodium alkyl amphopropionates such as sodium cocoamphopropionate, disodium alkyl amphodipropionate such as disodium cocoamphodipropionate, betaines, such as alkyl amino-betaines, alkyl dimethyl betaines and cocoamidopropyl betaine, imadazolines, sulfobetaines, sultaines, hydroxysultaines, alkyl iminoacetates, iminodialkanoates, aminoalkanoates, and mixtures thereof.

Another embodiment of the invention includes the addition of about 0.02 to about 2% of an emollient/emulsifier comprising a glycerol ester of a $C_8$-$C_{14}$ fatty acid. A preferred glycerol ester is glyceryl laurate (glycerol monolaurate). In addition to its advantages emollient and emulsifying properties, glycerol esters of fatty acids have sometimes been found to prevent bacterial growth in the formulation thereby preserving it.

Formulations of the invention especially body washes and soaps can also contain water. Typically such aqueous formulations contain from about 2 to about 95% water, preferably 10 to 90%. However, formulations of the invention can also be anhydrous.

Since the skin tends to be mildly acidic it is generally advisable to buffer formulations of the invention into a mildly acidic pH range to minimize irritation. An optimum pH range for formulations of the invention is from about 3.0 to about 7.0, more preferably 3.5 to 6.5.

The controlled release deodorizing and skin benefit salts are especially useful in deodorant formulations and can be used in combination with antiperspirant and other deodorant actives. The controlled release salts are formulated into either an antiperspirant or deodorant product matrix, wherein the salts are dispersed within the product matrix. In use, the product matrix containing the dispersed salts is applied to odiferous areas of the skin such as the underarm, so that the dispersed salts are spread or flow over the applied surface, where they deodorize and provide other skin benefits, such as soothing of the underarm skin, especially that which has been irritated due to damage by shaving. Once on the skin, the controlled-release salts partially dissolve and dissociate in sweat or other moisture on the underarm, thus allowing the controlled release salts to deliver both free cations and anions for deodorization and other possible skin benefits. The undissolved portion of the controlled release salt acts as a reservoir for further release of the deodorizing and skin benefit ions as they are depleted or washed away by the sweat.

It therefore another object of the present invention to provide a method for deodorization and perspiration control of the skin and potentially provide other benefits to the skin over an extended period of time. It is a further object of the present invention to provide a method of use for deodorizing skin using a formulation that contains controlled release salts dispersed with an antiperspirant in a deodorant matrix.

When present, antiperspirant actives are added at concentrations ranging from about 0.1% to about 30%, more preferably from about 5% to about 30%, by weight of the composition. The antiperspirant active can be solubilized or added as a solid, preferably in the form of dispersed solid particulates. Preferably the said dispersed particulate solids have an average particle diameter of less than about 100 microns, preferably from about 1 micron to about 40 microns.

The antiperspirant active for use in the antiperspirant embodiments of the present invention include any compound, composition or other material having antiperspirant activity. Preferred antiperspirant actives include astringent metallic salts, especially inorganic and organic salts of aluminum, zirconium and zinc, as well as mixtures thereof. Particularly preferred are aluminum-containing and/or zirconium-containing salts or materials, such as aluminum halides, aluminum hydroxyhalides, zirconyl oxyhalides, zirconyl hydroxyhalides, and mixtures thereof. Especially useful antiperspirant actives suitable for use in the formulations include aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered, and combinations thereof.

The antiperspirant and deodorant formulations of the present invention also comprise a solid suspending or thickening agent to help provide the formulations with the desired viscosity, rheology, texture and/or product hardness, or to otherwise help suspend any dispersed solids or liquids within the composition.

The term "suspending agent" as used herein, unless otherwise specified, means any material known or otherwise effective in providing suspending, gelling, solidifying and/or thickening properties to the composition or which otherwise provide structure to the final product form. These suspending agents include gelling agents, and polymeric or nonpolymeric or inorganic thickening agents.

The concentration and type of suspending agent selected for use in the antiperspirant and deodorant formulations will vary depending upon the desired product hardness, rheology, formulation (e.g., antiperspirant formulation or deodorant formulation) and/or other related product characteristics. For most suspending agents suitable for use herein, the total suspending agent concentration ranges from about 0.1% to about 40%, more typically from about 0.1% to about 35%, by weight of the composition. Suspending agent concentrations will tend to be lower for liquid embodiments (e.g., aerosols, roll-ons, etc) and higher for semi-solid (e.g., soft solids or creams) or solid stick embodiments.

Non limiting examples of suitable suspending agents include hydrogenated castor oil (e.g., Castorwax MP80, Castor Wax, etc.), fatty alcohols (e.g., stearyl alcohol), solid paraffins, triglycerides and other similar solid suspending esters or other microcrystalline waxes, silicone and modified silicone waxes. Non limiting examples of optional suspending agents suitable for use herein are described in U.S. Pat. No. 5,976,514 (Guskey et al.), U.S. Pat. No. 5,891,424 (Bretzler et al.), which descriptions are incorporated herein by reference.

Other suitable suspending agents include silicone elastomers at concentrations ranging from about 0.1% to about 10%, by weight of the composition. Non-limiting examples of such silicone elastomer materials suitable for use as a suspending agent herein are described in U.S. Pat. No. 5,654,362 (Schulz, Jr. et al.); U.S. Pat. No. 6,060,546 (Powell et al.) and U.S. Pat. No. 5,919,437 (Lee et al.), which descriptions are incorporated herein by reference.

Non-limiting examples of suitable suspending agents for use in deodorant embodiments of the present invention include fatty acid salts such as sodium stearate and other similar materials as described in U.S. Pat. No. 6,013,248 (Luebbe et al.), which description is incorporated herein by reference.

The anhydrous antiperspirant and deodorant formulations of the present invention optionally comprise an anhydrous carrier liquid at concentrations ranging from about 10% to about 99%, preferably from about 20% to about 70%, by weight of the composition. Such concentrations will vary depending upon variables such as product form, desired product hardness, selection of other ingredients in the composition, and so forth. The anhydrous carrier liquid for use in the composition can be any anhydrous liquid that is known for use in personal care applications or is otherwise suitable for topical application to the skin.

The carrier liquid can comprise a volatile or non-volatile silicone liquid, which may include cyclic, linear and/or branched chain silicones. The concentration of silicone liquids in the antiperspirant composition of the present invention preferably ranges from about 5% to about 80%, preferably from about 20% to about 60%, more preferably from about 30% to about 60%, by weight of the composition.

Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). Non limiting examples of suitable volatile silicones are described in Todd et al., "Volatile Silicone Fluids for Cosmetics", Cosmetics and Toiletries, 91:27-32 (1976), which descriptions are incorporated herein by reference.

Specific non limiting examples of suitable non volatile, linear, silicone carriers include Dow Corning 200, hexamethyldisiloxane, Dow Corning 225, Down Corning 1732, Dow Corning 5732, Dow Corning 5750 (available from Dow Corning Corp.); and SF-96, SF-1066 and SF18(350) Silicone Fluids (available from G. E. Silicones).

Many other carrier liquids known for use in personal care products can be used in the antiperspirant formulations, alone or in combination with the carrier liquids described in more detail herein. Many such other carrier liquids are disclosed in U.S. Pat. No. 6,013,248 (Luebbe et al.) and U.S. Pat. No. 5,968,489 (Swaile et al.), which descriptions are incorporated herein by reference.

The anhydrous antiperspirant and deodorant formulations of the present invention may further comprise any optional ingredient that is known for use in antiperspirants and deodorant products or other personal care products, or which is otherwise suitable for topical application to human skin.

Non limiting examples of optional ingredients include dyes or colorants, emulsifiers, perfumes, propellants, deodorant perfumes, preservatives, vitamins, non-vitamin nutrients, emollients, coupling agents or other solvents, surfactants, processing aides such as viscosity modifiers, wash-off aids, and so forth. Examples of such optional materials are described in U.S. Pat. No. 4,049,792 (Elsnau); U.S. Pat. No. 5,019,375 (Tanner et al.); and U.S. Pat. No. 5,429,816 (Hofrichter et al.); which descriptions are incorporated herein by reference.

The anhydrous antiperspirant and deodorant formulations of the present invention may be applied topically to the axilla or other area of the skin in an amount effective to treat or reduce perspiration wetness and/or malodor. The composition is preferably applied in an amount ranging from about 0.1 gram to about 20 grams, more preferably from about 0.1 gram to about 10 grams, even more preferably from about 0.1 gram to about 1 gram, to the desired area of the skin. The formulations are preferably applied one to two times daily, preferably once daily, to achieve effective antiperspirant and malodor control.

The anhydrous antiperspirant and deodorant formulations of the present invention can be formulated in a variety of product forms and then applied to the axilla or other area of the skin in the manner described herein, such variety product forms including solids (e.g., sticks), semi-solids (e.g., lotions, creams, soft solids), or liquids (e.g. aerosols, non-aerosol sprays, roll-ons, porous dome liquids).

Other ingredients, which can optionally be added to formulations of the invention include, but are not limited to, moisturizers, humectants, emollients, exfoliants, skin smoothing agents, neutraceuticals, vitamins, dyes fragrances, thickening agents, processing aids, preservatives and the like.

Skin cleaning and deodorant formulations of the invention can be used in any type of skin cleaning or body deodorization formulations, for example hand soaps, body washes, shampoos, pre-operation scrubs, wound cleaners, personal deodorants, antiperspirants, etc.

The following nonlimiting examples shall serve to illustrate the embodiments of the invention. The examples are presented solely for the purpose of illustration and are not to be construed as limitation on the present invention since many variations are possible without departing from the spirit and the scope of the invention. Unless otherwise stated, all parts and percentages are on a weight basis.

Example 1
Deodorant Stick

| Ingredient/Wt. % | |
|---|---|
| Sodium stearate | 8.0% |
| Water | 3.5 |
| Decanoate salt of N-lauroyl lysine ethyl ester | 3.0 |
| 1,3 propanediol | 15.0 |
| Glycerine | 5.0 |
| Ethanol | 62.0 |
| Hyaluronic acid | 1.0 |
| Essential oil fragrance | 0.5 |
| Sorbitan stearate | 2.0 |
| Total | 100.0. |

Example 2
Deodorizing Bath Oil

| Ingredient/Wt. % | |
|---|---|
| Isopropyl myristate | 20.0% |
| Mineral oil | 30.0 |
| Ethoxylated Glyceryl cocoate | 15.0 |
| Sodium lauroamphoacetate | 10.0 |
| Lauramidopropyl betaine | 8.0 |
| Polyquaternium-4 | 2.0 |
| Glyceryl monolaurate | 2.0 |

Example 2
Deodorizing Bath Oil

| Ingredient/Wt. % | |
| --- | --- |
| Octanoate salt of lauryl alanine ester | 2.0 |
| Lavender oil fragrance | 1.0 |
| Water | 10.0 |
| Total | 100.0 |

Example 3
Body wash

| Ingredient/Wt. % | |
| --- | --- |
| Cocoamidopropyl betaine | 15.0% |
| Carbomer salt of N-lauroyl arginine ethyl ester | 2.0 |
| Decyl glucoside | 10.0 |
| Guar hydroxypropyltrimonium chloride | 2.0 |
| Lactic acid | To pH 4.5-5.5 |
| Lemon fragrance | 0.5 |
| Water | 70.5 |
| Total | 100.0 |

What is claimed is:

1. A method for-cleaning or deodorizing the skin by the application of a formulation that deposits limited solubility undissociated controlled release salt on the surface of the skin, the formulation comprising:
   (1) from about 0.02 wt % to 5 wt % of a controlled release skin benefit or deodorizing salt with solubility of the salt in the moisture on the skin equal to or less than 1 wt % and greater than about 0.01 wt % comprising (i) a surface active cation and (ii) a carboxylate anion; and
   (2) from about 0.05% to about 20 wt % of a water absorbing hydrophilic polymer with a molecular weight above 2000; and
   optionally (3) from about 1% to about 90 wt % of an anionic, nonionic or amphoteric surfactant or soap; and
   optionally (4) buffers to provide a pH between about 3.0 and 7.0; and
   optionally (5) from about 2 wt % to about 95 wt % moisture; and
   optionally (6) from about 0.1 wt % to about 30 wt % of an antiperspirant active; and
   optionally (7) from about 0.1 wt % to about 40 wt % of a suspending agent; and
   optionally (8) from about 10 wt % to about 99 wt % of a carrier liquid, wherein said controlled release salt has sufficient solubility in the moisture on the skin to release an effective quantity of the skin benefit or deodorant ions but leaves undissolved salt to provide a reservoir of skin benefit ions for release as the dissolved ions are used up or dissipated.

2. The method of claim 1, in which the surface active cation is selected from the group consisting of a benzalkonium cation, a benzethonium cation, a cetylpyridinium cation, a chlorhexidinium cation, and Na-lauroyl arginine ethyl ester cation.

3. The method of claim 1 in which the carboxylate anion is a mono, di, or tri or polycarboxylate ion, or a polymeric carboxylate ion.

4. The method of claim 3 in which the mono-carboxylate anion is selected from the following group consisting of caproate, caprylate, laurate, myristate, palmitate, stearate, oleate, linoleate, linolenate, undecylenate, and retinoate.

5. The method of claim 1 in which the carboxylate anion is selected from the group consisting of salicylate and ascorbate.

6. The method of claim 3 in which the polymeric carboxylate anion is selected from the group consisting of a straight chain or cross-linked polyacrylate, an alginate, and a carboxylated cellulosic anion.

7. The method of claim 1, wherein the suspending agent is selected from the group consisting hydrogenated castor oils, fatty alcohols, solid paraffins, triglycerides, microcrystalline waxes, silicones, modified silicone waxes, silicone elastomers, sodium stearate, glycols, and other fatty acid salts.

8. The method of claim 1, in which the antiperspirant is selected from the group consisting of aluminum halides, aluminum chlorohydrate, aluminum hydroxyhalides, zirconyl oxyhalides, zirconyl hydroxyhalides aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered and combinations thereof.

9. The method of claim 1, wherein the carrier liquid is selected from the group consisting of volatile and non-volatile cyclic, linear, and branched chain silicone liquids.

10. The method of claim 1, in which the antiperspirant is selected from the group consisting of antihistamine salts.

* * * * *